United States Patent
Yi et al.

(10) Patent No.: US 10,473,878 B2
(45) Date of Patent: *Nov. 12, 2019

(54) STAND EQUIPPED WITH COUNTERBALANCE UNIT

(71) Applicants: KOHYOUNG TECHNOLOGY INC., Seoul (KR); INDUSTRY-UNIVERSITY COOPERATION FOUNDATION HANYANG UNIVERSITY ERICA CAMPUS, Ansan-si, Gyeonggi-do (KR)

(72) Inventors: Byung-Ju Yi, Bucheon-si (KR); Jong-Tae Seo, Ansan-si (KR)

(73) Assignees: KOHYOUNG TECHNOLOGY INC., Seoul (KR); INDUSTRY-UNIVERSITY COOPERATION FOUNDATION HANYANG UNIVERSITY ERICA CAMPUS, Ansan-si, Gyeonggi-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/372,882

(22) PCT Filed: May 23, 2014

(86) PCT No.: PCT/KR2014/004649
§ 371 (c)(1),
(2) Date: Jul. 17, 2014

(87) PCT Pub. No.: WO2014/189336
PCT Pub. Date: Nov. 27, 2014

(65) Prior Publication Data
US 2016/0252699 A1  Sep. 1, 2016

(30) Foreign Application Priority Data

May 24, 2013 (KR) .................. 10-2013-0059337
May 22, 2014 (KR) .................. 10-2014-0061915

(51) Int. Cl.
*A47F 5/00* (2006.01)
*G02B 7/00* (2006.01)
(Continued)

(52) U.S. Cl.
CPC .............. *G02B 7/001* (2013.01); *A61B 90/50* (2016.02); *F16M 11/06* (2013.01);
(Continued)

(58) Field of Classification Search
CPC .... G02B 7/001; F16M 11/2007; F16M 11/38; F16M 11/06; F16M 2200/063;
(Continued)

(56) References Cited

U.S. PATENT DOCUMENTS

D13,739 S    10/1855  Hunter
D142,263 S    8/1873  Morrison
(Continued)

FOREIGN PATENT DOCUMENTS

CN    2109175    7/1992
CN    2452453    10/2001
(Continued)

OTHER PUBLICATIONS

Naoyuki Takesue, "Gravity Compensation Mechanisms for Energy-Saving and Safety", JRSJ, vol. 29, No. 6, pp. 508-511, 2011.
(Continued)

*Primary Examiner* — Kimberly T Wood
(74) *Attorney, Agent, or Firm* — Kile Park Reed & Houtteman PLLC

(57) ABSTRACT

The present invention relates to a stand equipped with a counterbalance unit, i.e., a stand consisting of links, joints, a front link, and a counterbalance unit. Therefore, even when various medical apparatuses including such as a microscope, etc. are used, a stable counterbalance can be maintained and
(Continued)

the degree of freedom of movements of the medical apparatus can be easily adjusted according to the purpose of users.

12 Claims, 4 Drawing Sheets

(51) Int. Cl.
*A61B 90/50* (2016.01)
*F16M 11/06* (2006.01)
*F16M 11/20* (2006.01)
*F16M 11/38* (2006.01)

(52) U.S. Cl.
CPC ......... *F16M 11/2007* (2013.01); *F16M 11/38* (2013.01); *A61B 2090/504* (2016.02); *A61B 2090/506* (2016.02); *F16M 2200/041* (2013.01); *F16M 2200/063* (2013.01)

(58) Field of Classification Search
CPC ............ A61B 90/50; A61B 2090/5025; A61B 2090/504; A61B 2090/506
USPC ................ 248/123.2, 278.1, 280.11, 281.11; 359/384
See application file for complete search history.

(56) References Cited

U.S. PATENT DOCUMENTS

| | | | |
|---|---|---|---|
| 1,070,524 A | 8/1913 | Pieper | |
| 1,178,058 A | 4/1916 | Cruse | |
| 1,189,754 A | 7/1916 | Trenaman | |
| 4,339,100 A * | 7/1982 | Heller | F16M 11/08 248/123.2 |
| 5,173,802 A * | 12/1992 | Heller | F16M 11/08 359/384 |
| 5,186,422 A * | 2/1993 | Nakamura | F16M 11/123 248/123.2 |
| 5,480,114 A | 1/1996 | Nakamura | |
| 5,528,417 A * | 6/1996 | Nakamura | F16M 11/10 359/368 |
| 5,812,301 A * | 9/1998 | Nakamura | F16M 11/10 248/123.11 |
| 5,818,638 A * | 10/1998 | Nakamura | F16M 11/10 248/123.2 |
| 5,825,536 A * | 10/1998 | Yasunaga | F16M 11/105 248/123.11 |
| 6,105,909 A | 8/2000 | Wirth et al. | |
| 7,018,386 B2 * | 3/2006 | Nakamura | A61B 1/00149 359/384 |
| 7,461,824 B2 * | 12/2008 | Poxleitner | F16M 11/10 248/123.11 |
| 7,942,378 B2 * | 5/2011 | Nakamura | G02B 7/001 248/123.11 |
| 8,038,108 B2 * | 10/2011 | Yasunaga | A61B 90/50 248/123.2 |
| 9,364,290 B2 | 6/2016 | Yi et al. | |
| 2003/0151805 A1 | 8/2003 | Schmidt | |
| 2004/0172012 A1 | 9/2004 | Otsuka et al. | |
| 2004/0190131 A1 | 9/2004 | Brenner et al. | |
| 2008/0237413 A1 | 10/2008 | Hammer | |
| 2013/0140412 A1 | 6/2013 | Hirose | |

FOREIGN PATENT DOCUMENTS

| | | |
|---|---|---|
| DE | 197 42 051 | 3/1999 |
| DE | 93 21 575 | 1/2000 |
| EP | 0 023 003 | 1/1981 |
| EP | 0 419 070 | 3/1991 |
| EP | 0 609 085 | 8/1994 |
| JP | 6-197912 | 7/1994 |
| JP | 6-217993 | 8/1994 |
| JP | 7-227791 | 8/1995 |
| JP | 10-272143 | 10/1998 |
| JP | 11-28216 | 2/1999 |
| JP | 11-153293 | 6/1999 |
| JP | 2009-514633 | 4/2009 |
| WO | 2010/085901 | 8/2010 |
| WO | 2012/117922 | 9/2012 |

OTHER PUBLICATIONS

International Search Report for International Application No. PCT/KR2014/004649, dated Aug. 22, 2014.
Written Opinion with English Translation for International Application No. PCT/KR2014/004649, dated Aug. 22, 2014.
Japanese Notice of Allowance with English Translation for Japanese Patent Application 2017-021023, dated Feb. 5, 2019.
Chinese Office Action with English Translation for Chinese Patent Application 201710301720, dated Mar. 4, 2019.

* cited by examiner

[Fig. 1]
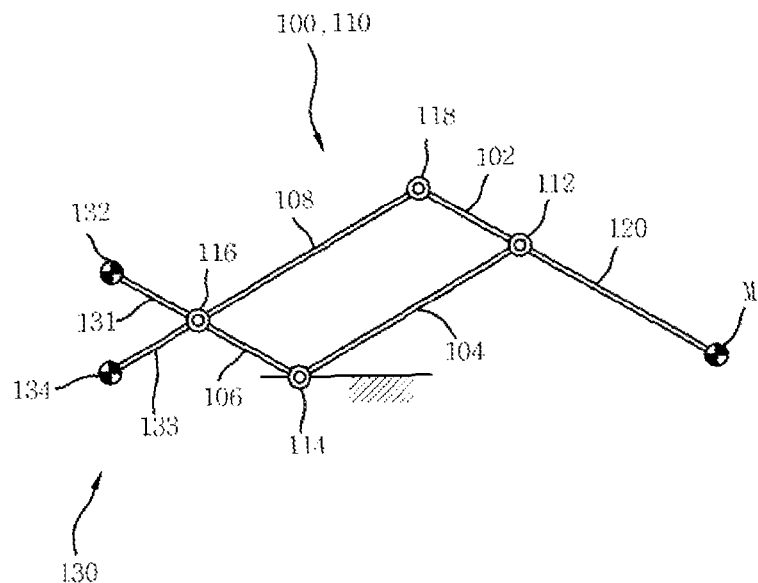
[Fig. 2]
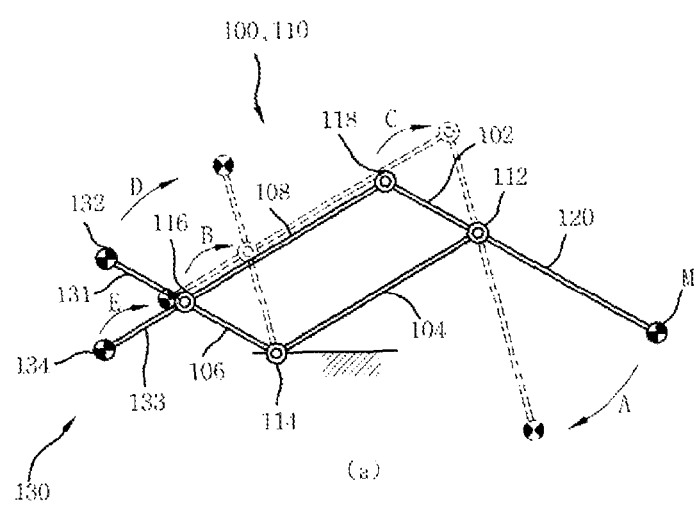
(a)
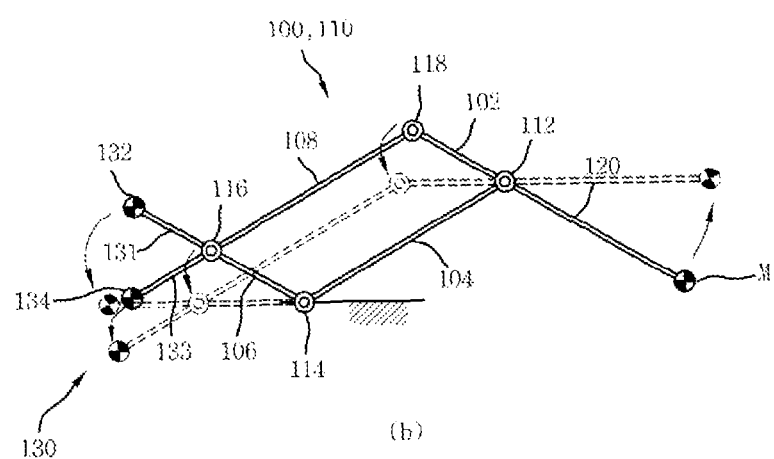
(b)

[Fig. 3]
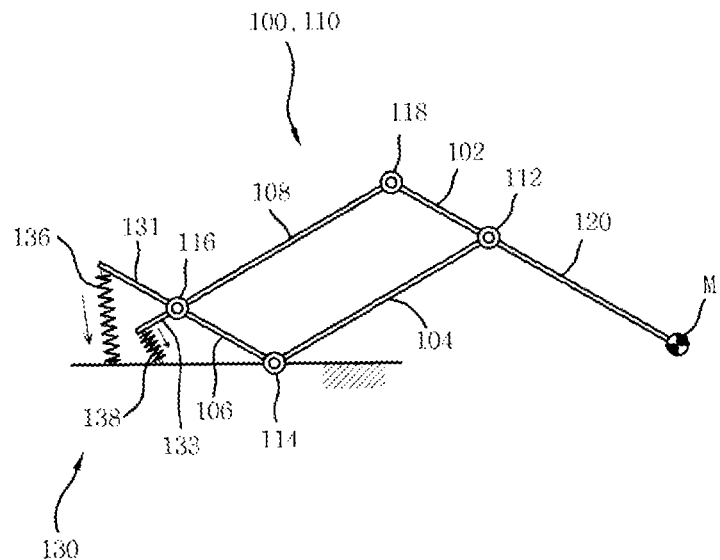
[Fig. 4]
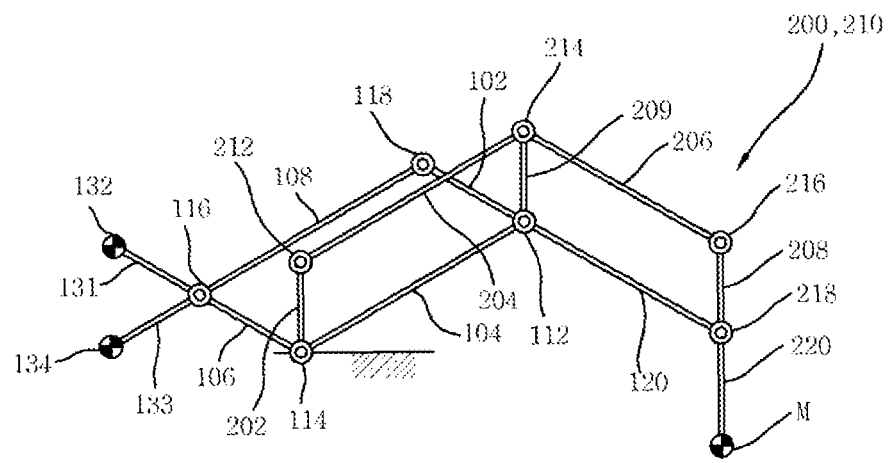
[Fig. 5]
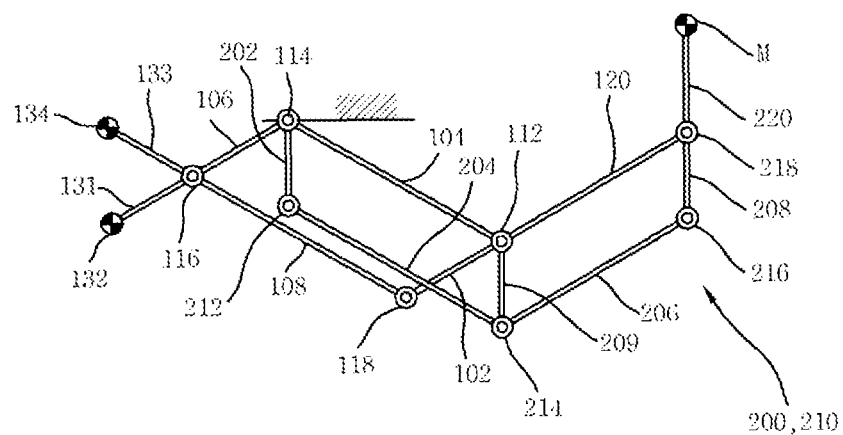

[Fig. 6]
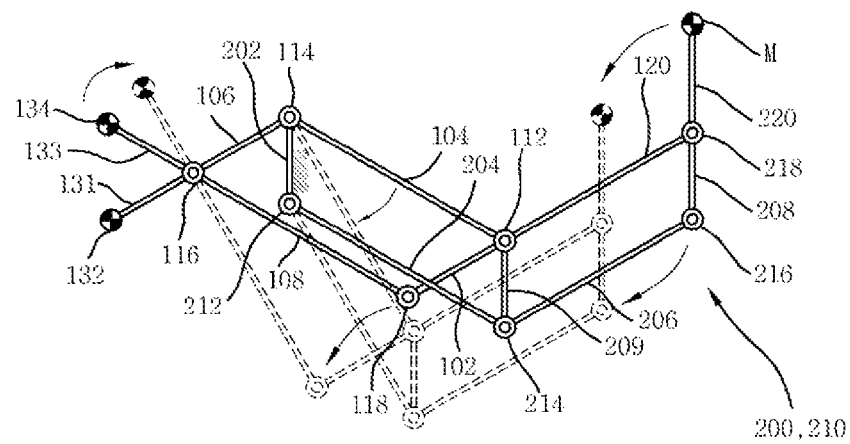
[Fig. 7]
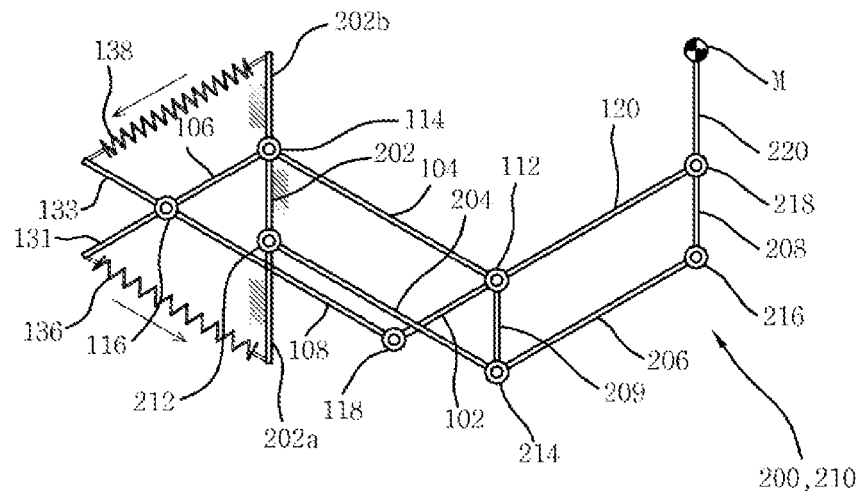

[Fig. 8]
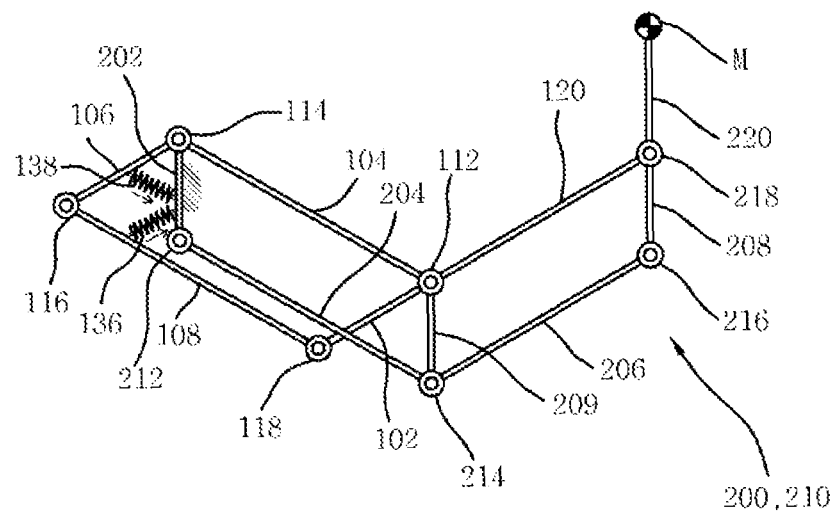
[Fig. 9]
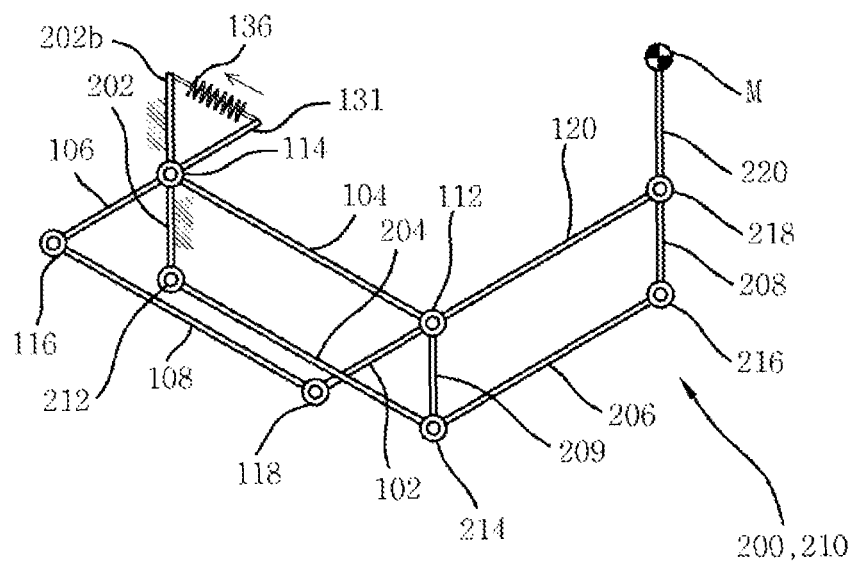

STAND EQUIPPED WITH COUNTERBALANCE UNIT

TECHNICAL FIELD

The present invention relates to a stand equipped with a counterbalance unit, more particularly, a stand equipped with a counterbalance unit wherein a medical apparatus such as a microscope and a surgical end effector can be installed and moved to a desired position.

BACKGROUND ART

Microsurgery, in which a medical surgical microscope is used to observe affected parts while performing surgery, has been studied and introduced in the surgical operation field.

In such microsurgery, a stand is needed to install weighty objects, i.e., a surgical microscope with its attached devices; place them in a desired space; then maintain their position.

Generally, in the balance structure of such a stand, the middle part of a link unit using a parallel link is rotatably connected to a holding unit, while a surgical microscope is installed at one end of the link unit and a counterweight is placed at the other end of the link unit, centered on the point of rotation, in order to offset the weight of the surgical microscope.

Since a surgical microscope is mounted with attachments such as an assistant scope or a video camera, etc., the position of a counterweight is adjusted based on the total weight of the surgical microscope to maintain the overall balance between the surgical microscope and the counterweight.

However, in case when a surgical microscope and its attached devices remain in the desired position, their vertical balance needs to be maintained, but a conventional stand has difficulties to control the vertical balance due to the inconsistent total weight of a surgical microscope by the presence of various attachments.

DISCLOSURE

Technical Problem

The present invention is devised to solve the problem stated above, therefore an object of the present invention is to provide a stand equipped with a counterbalance unit capable of maintaining a reliable and efficient counterbalance regardless positions of a medical apparatus.

Another object of the present invention is to provide a stand equipped with a replaceable counterweight based on the size of torque in joints caused by a medical apparatus, and a counterbalance unit capable of adjusting the length of a balance link.

The other object of the present invention is to provide a stand equipped with a counterbalance unit capable of enhancing degree of freedom easily.

Technical Solution

In order to achieve the objects herein, a stand equipped with a counterbalance unit according to the present invention is composed of the following technical properties: four links arranged in a square configuration; four joints that are connected to each connection part of the four links independently and enable these links to be mutually rotatable; a front link that is extended from an end of any one of the four links and mounted with a medical apparatus at the end; a counterbalance unit connected to a joint that is diagonally located from the joint from where the front link is extended.

Advantageous Effects

A stand equipped with a counterbalance unit according to the present invention can obtain a large torque compensation effect with small weight by optimizing the mounting position of counterbalance.

In addition, even when a number of medical apparatus such as a microscope and the like are used, because of a replaceable counterweight based on the size of torque in joints caused by a medical apparatus and a counterbalance unit capable of adjusting the length of a balance link, a reliable and efficient counterbalance can be maintained.

Moreover, depending upon the purpose of a user, multiple extension link members can be installed to improve the degree of freedom of the movement of a medical apparatus.

DESCRIPTION OF DRAWINGS

FIG. 1 is a schematic diagram illustrating a stand equipped with a counterbalance unit according to the present invention.

FIG. 2 is schematic diagrams illustrating FIG. 1 in operation modes.

FIG. 3 is a schematic diagram illustrating an embodiment of a counterbalance unit.

FIG. 4 is a schematic diagram illustrating a stand equipped with extension link members.

FIG. 5 is a schematic diagram illustrating another embodiment of FIG. 4.

FIG. 6 is schematic diagrams illustrating FIG. 5 in operation modes.

FIG. 7 to FIG. 9 are schematic diagrams illustrating various embodiments of a counterbalance unit.

BEST MODE

Hereinafter, more detailed description of a stand equipped with a counterbalance unit according to the present invention is provided by using appended drawings.

The present invention relates to a stand equipped with a counterbalance unit, wherein FIG. 1 is a schematic diagram illustrating a stand equipped with a counterbalance unit according to the present invention, FIG. 2 is schematic diagrams illustrating FIG. 1 in operation modes, and FIG. 3 is a schematic diagram illustrating an embodiment of a counterbalance unit.

A stand equipped with a counterbalance unit according to the present invention is composed of four links 100 arranged in a square configuration; four joints 110 that are connected to each connection part of the four links 100 independently and enable these links 100 to be mutually rotatable; a front link 120 that is extended from an end of any one of the four links 100 and mounted with a medical apparatus M at the end; a counterbalance unit 130 connected to a joint 110 that is diagonally located from the joint 110 from where the front link 120 is extended.

Each component is described in more details as follows.

Joints 110 consist of the first, second, third, and fourth joints 112, 114, 116, 118 and are connected to each connection part of the four links 100 independently so that the links 100 are mutually rotatable.

Links 100 consist of the first link 102 whose both ends are connected to the first and fourth joints 112, 118; the third link 106 whose both ends are connected to the second and third joints 114, 116 and placed on the opposite side of the first link 102; the second link 104 whose both ends are connected to the first and second joints 112, 114; the fourth link 108 whose both ends are connected to the third and fourth joints 116, 118 and placed on the opposite side of the second link 104. The links are arranged in a square configuration, but it is preferable to be arranged in a parallelogram configuration as illustrated in FIG. 1. For simplicity, the description hereinafter relates to an embodiment in which links 100 are arranged in a parallelogram configuration. In case of which links 100 are not formed in a parallelogram configuration, parallel can be understood as subtended.

Both ends of the first link 102 are connected to the first and fourth joints 112, 118, while the third link 106 located in parallel to the first link 102 has its both ends connected to the second and third joints 114, 116. In addition, both ends of the second link 104 are connected to the first and second joints 112, 114, while the fourth link 108 located in parallel to the second link 104 has its both ends connected to the second and third joints 114, 116. Accordingly, the first, second, third, and fourth links 102, 104, 106, 108 are mutually rotatable and thus a medical apparatus M which will be described later is to have the degree of freedom.

Meanwhile, four joints 110 has at least any one of them fixed to a holding unit (not shown) to be supported, and in case of an embodiment of the present invention, the second joint 114 is fixed to a holding unit to be supported.

A front link 120, extended from any one end of the four links 100 and mounted with a medical apparatus M at the end, moves the medical apparatus M according to the movement of the links 100 which is interlocked to the front link. In the embodiment of the present invention, it is set to be that a front link 120 is extended from an end of the first link 102 as illustrated in FIG. 1, and the first joint 112 is connected between the first link 102 and the front link 120.

A counterbalance unit 130 is connected to a joint 110 placed in a diagonal direction from the joint 110 that is located at the extension part from where a front link 120 is extended, and functions to counterbalance a medical apparatus M. That is, according to the embodiment of links 100, as illustrated in FIG. 1, the first joint 112 is placed at the extension part from where a front link 120 is extended, and the third joint 116 is positioned in the diagonal direction from the first joint 112, thus a counterbalance unit 130 is connected to the third joint 116.

The counterbalance unit 130 in the present invention can use weighter and springs to balance against a front link 120 with a medical apparatus M. Hereinafter, the description of the case using weighter will come first.

A counterbalance unit 130 is composed of two links 100 connected to the third joint 116, i.e., the first and second balancing links 131, 133 extended from the third and fourth links 106, 108; the first and second counterweights 132, 134 independently mounted at the end of the first and second balancing links 131, 133. Accordingly, the first and second counterweights 132, 134 are placed on the opposite side of a medical apparatus M, centering the second joint 114, to maintain balance, and in case when the medical apparatus M moves to the direction contrary to gravity, the first and second counterweights 132, 134 move to the direction of gravitational force in order to compensate the torque in joints caused by the medical apparatus. Since a counterbalance unit 130 is connected to the third joint 116 as illustrated in FIG. 1 instead of to the second joint 114 that is functioning as the central axis, the effective distance to the central axis (the distance between the central axis and the gravity vector functioning in the counterweights) is maximized in most movements of links 100, and thus the torque in joints generated by the medical apparatus can be compensated in full.

Meanwhile, the length of the first and second balancing links 131, 133 is adjustable, and each of the first and second counterweights 132, 134 is removably installed on the first and second balancing links 131, 133 respectively, thus the compensated torque in joints can be controlled in accordance with the length of a front link 120 or the weight of a medical apparatus M.

A counterbalance unit 130 in another embodiment is composed of the first and second balancing links 131, 133 extended from the third and fourth links 106, 108; the first and second counter springs 136, 138 attached to the tip of the first and second balancing links 131, 133 respectively. For reference, a holding unit fixing the second joint 114 is extended in parallel with the ground. And as illustrated in FIG. 3, one end of the first counter spring 136 is connected to the tip of the first balancing link 131, while the other end is connected to the holding unit. In this case, the first counter spring 136 is a tension spring that moves the first balancing link 131 to gravity direction which is the direction of the arrow in order to compensate the torque in joints generated by a medical apparatus M. One end of the second counter spring 138 is connected to the tip of the second balancing link 133, while the other end is connected to the holding unit. The second counter spring 138 is also a tension spring and it moves the second balancing link 133 to the direction of the arrow in order to compensate the torque in joints generated by a medical apparatus M.

Also, one end of the counter spring can be connected to the third link 106, while the other end is connected to the holding unit when necessary.

Hereinafter, the operation mode of a stand equipped with a counterbalance unit according to the present invention will be described by using appended drawings.

Referring to FIG. 2(*a*), when a medical apparatus M moves to the direction A complying with gravity, due to the structure of links 100, each of the third and fourth joints 116, 118 moves to the direction B and C respectively, therefore, the first and second counterweights 132, 134 independently move to the direction D and E contrary to the direction of gravity. Consequently, the potential energy of the first and second counterweights 132, 134 increases, therefore, less force is required for the medical apparatus M to return to its original position or move to other positions as illustrated in FIG. 2(*b*).

Conversely as illustrated in FIG. 2(*b*), when a medical apparatus M moves to a direction against gravity, the links 100 function to the opposite direction from FIG. 2(*a*), which leads the first and second counterweights 132, 134 to move conforming to gravity, thus decreases the potential energy while enabling to move the medical apparatus M against gravity using only little force.

FIG. 4 is a schematic diagram illustrating a stand equipped with extension link members; FIG. 5 is a schematic diagram illustrating another embodiment of FIG. 4; FIG. 6 is schematic diagrams illustrating FIG. 5 in operation modes.

Extension link members are composed of extension links 200 connected to links 100 and a front link 120; extension joints 210 connected to each connection part of the extension links 200 respectively and capable of extension links 200 to be mutually rotatable; an extension front link 220 extended from an end of the extension link 200 that is one of extension links 200 and connected to the front link 120, thereby function to improve the degree of freedom of a medical apparatus M.

Extension joints 210 are composed of the first, second, third, and fourth extension joints 212, 214, 216, 218.

Extension links 200 are placed on the opposite side of the second link 104 and composed of the second extension link 204 whose both ends are connected to the first and second extension joints 212, 214; the third extension link 206 placed on the opposite side of a front link 120 and having its one end connected to the second extension joint 214 while the other end is connected to the third extension joint 216; the first extension link 202 whose both ends are independently connected to the second joint 114 and the first extension joint 212; the fourth extension link 208 whose one end is connected to the third extension joint 216 while the other end is connected to the fourth extension joint 218; the fifth extension link 209 whose both ends are independently connected to the first joint 112 and the second extension joint 214.

In extension link members illustrated in FIG. 4, each of the second and third extension links 204, 206 is placed in parallel with the second link 104 and a front link 120 respectively, and one ends of the second and third extension links 204, 206 are connected to each other through the second extension joint 214, while the other end of the second extension link 204 is connected to the first extension joint 212 and the other end of the third extension link 206 is connected to the third extension joint 216. In addition, the both ends of the first extension link 202 are connected to the second joint 114 and the first extension joint 212, and the both ends of the fourth extension link 208 are connected to the third extension joint 216 and the fourth extension joint 218, while the both ends of the fifth extension link 209 are connected to the first joint 112 and the second extension joint 214. That is, extension links 200 having the shape of two overlapped parallelograms are extended from the center point that is the second joint 114.

Also, the first extension link 202 can be fixed perpendicularly to the installation surface in order to maintain an extension front link 220, which will be described later, to be vertical. In other words, since the first extension link 202 and the fifth extension link 209 are always in parallel while the fifth extension link 209 and the fourth extension link 208 are always in parallel, an extension front link 220 extended from the fourth extension link 208 is likewise in parallel with the first extension link 202 all the time. Accordingly, in case of which a medical apparatus M such as a microscope should always remain vertical, the medical apparatus M can always remain vertical by fixing the first extension link 202 perpendicularly to the installation surface.

An extension front link 220 is extended from the fourth extension link 208, and has a medical apparatus M mounted at the tip of it. After all, extension links 200 are the supplementary means to bring the connection of the extension front link 220 and it is the extension front link 220 that interlocks the medical apparatus M with movements of links 100 as well as movements of extension link members to increase the degree of freedom.

Meanwhile, as illustrated in FIG. 5, a stand equipped with a counterbalance unit according to the present invention can be formed in the shape in which the top and the bottom of FIG. 4 are inverted. In case when a medical apparatus M functions from bottom to top, e.g., such as an objective lens of a microscope is in use, similarly, as illustrated in FIG. 6(a) and FIG. 6(b), the first extension link 202 can be fixed perpendicularly towards the ground in order for the extension front link 220 always to remain vertical while moving.

FIG. 7 to FIG. 9 are schematic diagrams illustrating various embodiments of a counterbalance unit.

Hereinafter, a stand equipped with extension link members with the application of counter springs is described using appended drawings.

First, referring to FIG. 7, there provided the first and second balancing links 131, 133 extended from the third and fourth links 106, 108; the first and the second auxiliary links 202a, 202b extended from the first extension link 202, and the first and second auxiliary links 202a, 202b are fixed perpendicularly towards the ground like the first extension link 202. And one end of the first counter spring 136 is connected to the tip of the first balancing link 131, while the other end is connected to the first auxiliary link 202a. In this case, the first counter spring 136 is a tension spring and moves the first balancing link 131 to the gravitational direction, i.e. the direction of the arrow, to compensate torque in joints created by a medical apparatus M. The one end of the second counter spring 138 is connected to the tip of the second balancing link 133, while the other end is connected to the second auxiliary link 202b. In this case, the second counter spring 138 is a tension spring and moves the second balancing link 133 to the direction of the arrow to compensate torque in joints created by a medical apparatus M.

Referring to FIG. 8 as another embodiment, one end of the first counter spring 136 is connected to the fourth link 108, while the other end is connected to the first extension link 202. One end of the second counter spring 138 is connected to the third link 106, while the other end is connected to the first extension link 202. The first and second counter springs 136, 138 are tension springs and each of them moves the fourth link 108 and the third link 106 to the directions of the arrows respectively to compensate torque in joints created by a medical apparatus M.

Referring to FIG. 9 as the other embodiment, the second auxiliary link 202b is extended from the first extension link 202, and the first balancing link 131 is extended from the third link 106 connected to the second joint 114. One end of the first counter spring 136 is connected to the first balancing link 131, while the other end is connected to the second auxiliary link 202b. In this case, the first counter spring 136 is a tension spring, and moves the first balancing link 131 to the direction of the arrow to compensate torque in joints created by a medical apparatus M.

Thus, in case of which counter springs are applied to a stand equipped with extension link members, various embodiments can be configured. For the greater variety of embodiments, counter springs that are directly connected to links 100 or extension links 200 as well as additional balancing links upon the necessity can be provided.

Meanwhile, more extension link members can be mounted upon the necessity. An additional link is connected to the second joint 114 supported by a holding unit; a link is connected in parallel with the second link 104; more links are connected, wherein each of the links is in parallel with a front link 120 and an extension front link 220 respectively. Next, an additional front link is connected to the extension front link 220 and then a medical apparatus is mounted at the tip of the connected front link. In the same manner as above, N number of extension link members can be additionally mounted in order to variously set the degree of freedom of medical apparatus.

And as the number of extension link members increases, a medical apparatus M gets further from the second joint 114 that is the center point of rotation, accordingly, the torque in joints generated by the medical apparatus M grows bigger.

In order to maintain a stable counterbalance, it is desirable that the length of the first and second balancing links 131, 133 increases proportion to the growing number of extension link members. For the efficient counter balance, it is more preferable to increase the weight of the first and second counterweights 132, 134 as well as the length of the first and second balancing links 131, 133.

DETAILED DESCRIPTION OF MAIN ELEMENTS

100: link
102: the first link
104: the second link
106: the third link
108: the fourth link
110: joint
112: the first joint
114: the second joint
116: the third joint
118: the fourth joint
120: front link
130: counterbalance unit
131: the first balancing link
132: the first counterweight
133: the second balancing link
134: the second counterweight
136: the first counter spring
138: the second counter spring
200: extension link
202: the first extension link
202a: the first auxiliary link
202b: the second auxiliary link
204: the second extension link
206: the third extension link
208: the fourth extension link
209: the fifth extension link
210: extension joint
212: the first extension joint
214: the second extension joint
216: the third extension joint
218: the fourth extension joint
220: extension front link

The invention claimed is:

1. A stand, comprising:
a first link, second link, a third link, and a fourth link arranged in a parallelogram configuration;
a first joint, a second joint, a third joint, and a fourth joint, each of the first joint, the second joint, the third joint, and the fourth joint being connected to each connection part of the first link, the second link, the third link, and the fourth link, respectively, and enabling the first link, the second link, the third link, and the fourth link to be mutually rotatable, wherein the second joint between the second link and the third link is fixed to a holding unit and the second joint and the fourth joint are arranged in a diagonal direction;
a front link extended from the first link in a direction from the fourth joint toward the first joint;
a counterbalance unit connected to the third joint;
a first extension link connected to the second joint;
a first extension joint arranged at an end of the first extension link;
a second extension link extended from the first extension joint in parallel with the second link;
a second extension joint arranged at an end of the second extension link;
a third extension link extended from the second extension joint in parallel with the front link;
a third extension joint arranged at an end of the third extension link;
a fourth extension joint arranged at an end of the front link;
a fourth extension link arranged between the third extension joint and the fourth extension joint; and
a fifth extension link arranged between the first joint and the second extension joint,
wherein the first extension link, the fourth extension link and the fifth extension link are in parallel with one another,
wherein a first parallelogram includes the first extension link, the second extension link, the fifth extension link, and the second link,
wherein a second parallelogram includes the front link, the third extension link, the fourth extension link, and the fifth extension link, and
wherein the first parallelogram is connected to the second parallelogram through the first joint, the second extension joint, and the fifth extension link.

2. The stand of claim 1, further comprising an extension front link extended from the fourth extension link.

3. The stand of claim 1, wherein the counterbalance unit comprises first and second balancing links and first and second counterweights mounted at tips of the first and second balancing links, respectively.

4. The stand of claim 3, wherein the first and second balancing links are connected to the third joint, and each of the first and second balancing links is extended from the third and fourth links, respectively.

5. The stand of claim 1, wherein the first extension link is fixed to the holding unit.

6. The stand of claim 2, wherein the counterbalance unit comprises first and second balancing links and first and second counterweights mounted at tips of the first and second balancing links, respectively.

7. A stand unit, comprising:
a first link, a second link, a third link, and a fourth link arranged in a first parallelogram;
a first joint, a second joint, a third joint, and a fourth joint, each of the first joint, the second joint, the third joint, and the fourth joint are connected to each connection part of the first link, the second link, the third link, and the fourth link, respectively, and enabling each of the first link, the second link, the third link, and the fourth link to be mutually rotatable, wherein the second joint between the second link and the third link is fixed to a holding unit and the second joint and the fourth joint are arranged in a diagonal direction;
a front link extended from the first link in a direction from the fourth joint toward the first joint;
a counterbalance unit connected to the third joint; and
a first extension link, a second extension link, a third extension link, a fourth extension link, and a fifth extension link,
wherein the first extension link, the second extension link, the fifth extension link, and the second link are arranged in a second parallelogram,
wherein the front link, the third extension link, the fourth extension link, and the fifth extension link are arranged in a third parallelogram,
wherein the second link of the second parallelogram and the front link of the third parallelogram are connected to the first joint, wherein the fifth extension link is shared between the second parallelogram and the third parallelogram and connects the first joint to an extension joint connecting the second extension link of the second parallelogram to the third extension link of the third parallelogram.

8. The stand of claim 7, further comprising an extension front link extended from the fourth extension link.

9. The stand of claim 7, wherein the counterbalance unit comprises first and second balancing links and first and second counterweights mounted at tips of the first and second balancing links, respectively.

10. The stand of claim 9, wherein the first and second balancing links are connected to the third joint, and each of the first and second balancing links is extended from the third and fourth links, respectively.

11. The stand of claim 7, wherein the first extension link is fixed to the holding unit.

12. The stand of claim 8, wherein the counterbalance unit comprises first and second balancing links and first and second counterweights mounted at tips of the first and second balancing links, respectively.

* * * * *